United States Patent [19]

Lehmann et al.

[11] Patent Number: 4,694,096
[45] Date of Patent: Sep. 15, 1987

[54] (ACYLTHIOPROPYL)PHENOLS

[75] Inventors: Hans Lehmann, Aesch; Abdul-Cader Zahir, Oberwil, both of Switzerland

[73] Assignee: Ciba-Geigy Corporation, Ardsley, N.Y.

[21] Appl. No.: 823,230

[22] Filed: Jan. 28, 1986

[30] Foreign Application Priority Data

Feb. 1, 1985 [CH]   Switzerland ............................. 452/85

[51] Int. Cl.[4] .......................................... C07C 153/023
[52] U.S. Cl. .................................... 558/251; 525/481; 525/104; 525/99
[58] Field of Search ......................................... 558/251

[56] References Cited

U.S. PATENT DOCUMENTS

| | | | |
|---|---|---|---|
| 4,127,615 | 11/1978 | Zahir et al. | 558/251 |
| 4,130,600 | 12/1978 | Zahir et al. | 558/251 |
| 4,371,719 | 2/1983 | Zahir et al. | 558/251 |
| 4,384,129 | 5/1983 | Zahir et al. | 558/251 |

OTHER PUBLICATIONS

R. Q. Brewster and W. E. McEwen, "Organic Chemistry", 3rd Ed, Prentice-Hall, Englewood Cliffs, 1961, p. 602.

J. D. Roberts and M. C. Caserio, ;37 Basic Principles of Organic Chemistry", Benjamin, New York, 1965, p. 907.

*Primary Examiner*—Henry R. Jiles
*Assistant Examiner*—Robert C. Whittenbaugh
*Attorney, Agent, or Firm*—Luther A. R. Hall

[57] ABSTRACT

Compounds of formula I or II

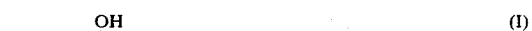

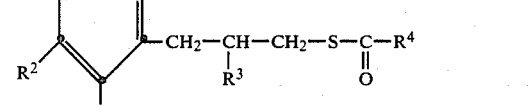

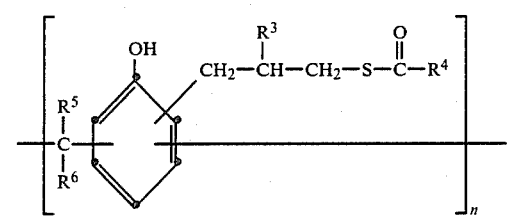

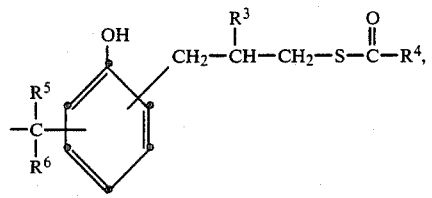

wherein $R^1$ and $R^2$ are hydrogen, alkyl, cyclohexyl, phenyl, benzyl or tolyl, or are a —$CH_2$—$CHR^3$—$CH_2$—S—CO—$R^4$ radical, $R^3$ is hydrogen or methyl, $R^\alpha$ is alkyl, cyclohexyl, phenyl, benzyl or tolyl, X is alkylene, —S—, —SO—, —$SO_2$— or substituted alkylene, in which $R^5$ and $R^6$ are hydrogen or alkyl, and n is an integer from 1 to 10, can be used as latent hardeners for epoxy resins.

The compositions containing epoxy resins and these hardeners are particularly suitable for use as single component adhesive formulations. The cured products have good hot water resistance.

7 Claims, No Drawings

(ACYLTHIOPROPYL)PHENOLS

The present invention relates to (acylthiopropyl)-polyphenyls, to the separation thereof, to compositions containing a curable epoxy resin and said polyphenols, to the use of said compositions as single component adhesive formulations and to the cured products obtained therefrom.

Epoxy resins are well known in the art and are reacted with a wide range of different hardeners to form cured products. For many applications it is desirable to have available an epoxy resin composition which can be readily cured and which is sufficiently storage stable to enable it to be mixed before use. It is therefore essential that the components, i.e. the epoxy resin and the hardener, are able to co-exist for reasonable periods of time after they have been mixed.

Many known hardeners which would produce effective and rapid curing at elevated temperatures are inadequate for this purpose, as they do not meet this requirement and, when incorporated into the epoxy resin, have a propensity to induce gelation.

To solve this problem, considerable efforts have been made to develop latent hardeners, i.e. hardeners that do not react with the resins at room temperature but which do react rapidly with them at elevated temperature.

The provision of such latent hardeners makes it possible to prepare epoxy resin compositions which are storage stable for considerable periods of time and, at the same time, are able to effect rapid curing upon heating.

Mercaptans and phenols are known for epoxy resins. Up to now no attempt has been made to combine both functional groups in one molecule and, furthermore, to provide the thiol group with a protective group. A suitably chosen protective group splits off under the reaction conditions of curing, so that both reactive groups are available for the curing step.

o-Acylthiopropylphenols are disclosed as pesticides in U.S. Pat. No. 3,443,012, but no mention is made therein of a utility as hardeners. Moreover, the compounds of this reference are mononuclear monophenols.

The present invention relates to compounds of formulae I and II

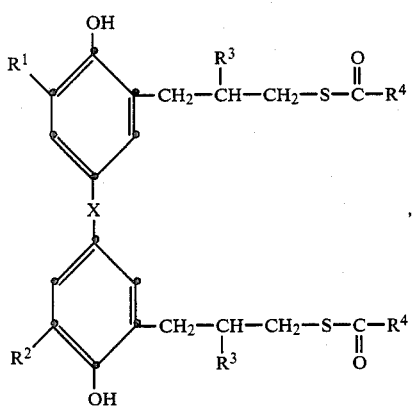

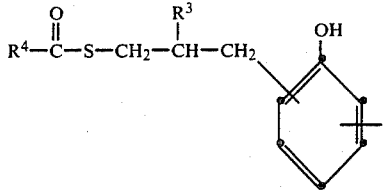

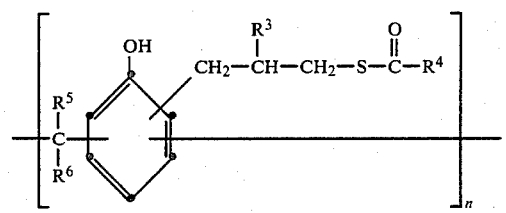

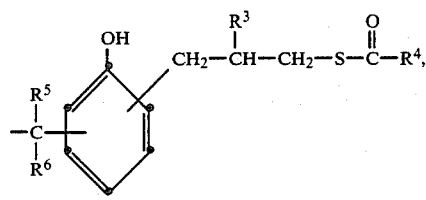

wherein $R^1$ and $R^2$ are each independently of the other hydrogen, $C_1$-$C_{18}$alkyl, cyclohexyl, phenyl, benzyl or tolyl, or are a —$CH_2$—$CHR^3$—$CH_2$—CO—$R^4$ radical, $R^3$ is hydrogen or methyl, $R^4$ is $C_1$-$C_{18}$alkyl, cyclohexyl, phenyl, benzyl or tolyl, X is —$CR^5R^6$—, —S—, —SO—, —$SO_2$— or —($CH_3$)C[—($CH_2$-$)_m$—$COOR^7$]—, in which $R^5$ and $R^6$ are each independently of the other hydrogen or $C_1$-$C_6$alkyl, $R^7$ is $C_1$-$C_{18}$-alkyl, m is 1 or 2 and n is an integer from 1 to 10.

$R^1$, $R^2$, $R^4$ and $R^7$ as $C_1$-$C_{18}$alkyl are straight chain or branched, preferably straight chain, radicals. Illustrative of such radicals are methyl, ethyl, propyl, isopropyl, n-butyl, sec-butyl, tert-butyl, n-pentyl, n-hexyl, n-heptyl, n-octyl, n-nonyl, n-decyl, n-dodecyl, n-tetradecyl, n-hexadecyl or n-octadecyl, as well as 1,1,3,3-tetramethylbutyl or 2-ethyl-n-hexyl.

Short and straight chain $C_1$-$C_6$alkyl radicals are preferred, with methyl being most preferred.

$R^5$ and $R^6$ as $C_1$-$C_6$alkyl may be methyl, ethyl, n-propyl, n-butyl, n-pentyl or n-hexyl, with methyl being preferred.

Preferred compounds of formulae I and II are those in which $R^3$ is hydrogen.

Particularly interesting compounds of formula I are those wherein $R^1$ and $R^2$ are each independently of the other hydrogen or $C_1$-$C_{12}$alkyl, $R^3$ is hydrogen, $R^4$ is $C_1$-$C_4$alkyl, X is a —$CR^5R^6$ group, in which $R^5$ and $R^6$ are each independently of the other hydrogen or methyl.

Interesting compounds of formula I are also those wherein $R^1$, $R^2$ and $R^3$ are hydrogen, $R^4$ is methyl and X is a group selected from —$CH_2$—, —$CH(CH_3)$— or —$C(CH_3)_2$—.

Particularly preferred compounds of formula I are those wherein $R^1$ and $R^2$ are each independently a —$CH_2$—$CHR^3$—$CH_2$—S—CO—$R^4$ group.

Of especial interest are also compounds of formula II, wherein $R^3$ is hydrogen, $R^4$ is methyl, —$CR^5R^6$— is a group selected from —$CH_2$—, —$CH(CH_3)$— or —$C(CH_3)_2$—, and n is an integer from 1 to 4.

The —CH$_2$—CHR$^3$—CH$_2$—S—CO—R$^4$ and —CR$^5$-R$^6$— groups in the novolak of formula II are preferably ortho- or para-positioned with respect to the phenolic hydroxyl group. The —CH$_2$—CHR$^3$—S—CO—R$^4$ groups are most preferably in the ortho-position.

R$^1$ and R$^2$ are preferably hydrogen or methyl, with hydrogen being most preferred.

R$^3$ is preferably hydrogen and R$^4$ is preferably methyl.

X is preferably —CH$_2$— or —C(CH$_3$)$_2$—, but is most preferably —C(CH$_3$)$_2$—.

Further preferred meanings of the group X are —S— or —SO$_2$— or —(CH$_3$)C[—CH$_2$—COOH$_3$]— or —(CH$_3$)C[—CH$_2$—CH$_2$—COOCH$_3$]—.

The compounds of formula I or II can for example be prepared by reacting a compound of formula III or IV

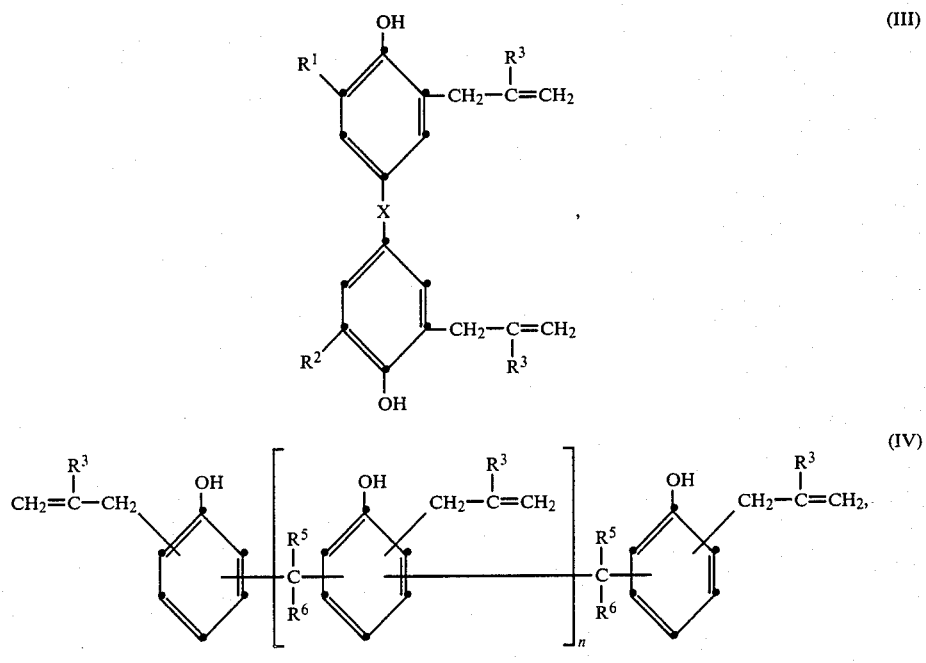

with a molar amount of a thiocarboxylic acid of formula V

which is substantially proportionate to the content of allylic double bonds, in the presence of a free radical generator. In the formulae III, IV and V above, R$^1$, R$^2$, R$^3$, R$^4$, R$^5$, R$^6$ and X, as well as the index n, have the meanings as defined above, except that in this case R$^1$ and R$^2$ are —CH$_2$—CR$^3$=CH$_2$ instead of —CH$_2$—CH-R$^3$—CH$_2$—S—CO—R$^4$.

The bis- or poly(meth)allylphenols of formula III or IV are known compounds or they can be prepared by methods which are known per se.

The thiocarboxylic acids of formula V are also known compounds and can likewise be obtained by methods which are known per se. A preferred process comprises reacting a suitable carboxylic acid anhydride, preferably acetic anhydride, with hydrogen sulfide or a water-soluble metal sulfide, in alkaline aqueous solution, isolating the resultant mixture of carboxylic acid and thiocarboxylic acid and using it, without further separation, in the subsequent reaction with the allylphenol or methylallylphenol.

The amount of thiocarboxylic acid V employed will depend on the number of allyl or methallyl groups in the starting material III or IV. As a rule, equimolar amounts of thiocarboxylic acid are used, based on the allyl groups. However, it is entirely possible to use an excess or a less than equivalent amount of thiocarboxylic acid.

Use of a less than equivalent amount of thiocarboxylic acid will result in only a partial reaction of the allyl groups of compounds III or IV. Such partially thioacylated products, especially partially reacted novolaks IV, also fall within the scope of this invention. These partially thioacylated novolaks IV are mixtures of compounds of different chain length and differing degree of thioacylation. On average, at least 50% of the allyl groups should be reacted.

The reaction to give the final product I or II is induced by radical initiation. This radical initiation is achieved e.g. by exposing the reaction mixture, if desired in the presence of a catalyst, to irradiation with shortwave light, or by heating the mixture, preferably in the presence of a free radical generator. However, the reaction may also be carried out purely thermally, preferably in the presence of a free radical generator.

Illustrative of free radical generators are organic peroxides such as benozyl peroxides, acetyl peroxide or cumyl hydroperoxide and, in particular, azo compounds. Preferred azo compounds are in particular those in which the azo group is attached on both sides to tertiary carbon atoms which, in addition to carrying alkyl groups, also carry nitrile or ester groups. An important representative of this class of compound is thus e.g. α,α-azobisisobutyronitrile (AIBN).

Exemplary of catalysts which may, if desired, be suitably used for the photoinitiation reaction are benzoin ethers, benzile ketals, ω-dialkoxyacetophenone derivatives or aromatic ketone/amine combinations.

The amount of free radical generator which may be employed is not crucial and may vary within wide limits. It is preferably less than 10 mol % of the number of allyl or methallyl groups in the reaction mixture.

The reaction of compound III and V or IV and V can be carried out in the presence or absence of a solvent.

If a solvent is employed it must be inert to the reactants and able to dissolve them. Examples of suitable solvents are therefore aliphatic or aromatic hydrocarbons such as hexane, benzene, toluene or xylene; or chlorinated hydrocarbons such as dichloromethane or chlorobenzene; and also ethers such as dioxane or diethyl ether; or aprotic solvents such as dimethylformamide. Depending on the mode of reaction and on the reactants, the reaction temperature is normally in the range from $-10°$ to $+250°$ C.

It is preferred to carry out initiation of the reaction of the allylphenol with the thiocarboxylic acid purely thermally, in the temperature range from 40° to 80° C. in an inert gas, for example $N_2$, in the absence of a solvent and in the presence of a free radical generator. The radical generator employed in this process variant is preferably azobisisobutyronitrile, although other radical generators are also suitable for the purpose. If azobisisobutyronitrile is used, the yield of acylthiopropyl compound is particularly high.

The phenols of this invention can be isolated from the reaction mixture in conventional manner, for example by distillation or fractional crystallation or by extraction, preferably with an aqueous alkaline solution.

The compounds of formula I and II can be employed as latent hardeners for eposy resins.

Accordingly, the invention also relates to compositions comprising
(a) an epoxy resin containing more than one epoxy group in the molecule or a still fusible and/or soluble curable precondensate of said epoxy resin (B-stage), and
(b) at least one compound of formula I and/or II, and
(c) further optional conventional auxiliaries such as a catalyst (curing accelerator), and to the cured products which can be obtained therefrom by heating.

Preferred compositions are those comprising (a) the epoxy resin and (b) at least one compound of formula I.

The epoxy resins to be employed preferably contain more than one epoxy group in the molecule. Such compounds are in particular: alicyclic polyepoxides such as epoxyethyl-3,4-epoxycyclohexane, vinylcyclohexene diepoxide, limonene diepoxide, dicyclopentadiene diepoxide, bis(3,4-epoxycyclohexylmethyl)adipate, (3',4'-epoxycyclohexylmethyl)-3,4-epoxycyclohexanecarboxylate, 3',4'-epoxy-6'-methylcyclohexylmethyl-3,4-epoxy-6-methylcyclohexanecarboxylate, 3-(4',4'-epoxycyclohexyl)-2,4-dioxaspiro[5,5]-8,9-epoxyundecane, 3-(glycidyloxyethoxyethyl)-2,3-dioxaspiro-[5.5]-8,9-epoxyundecane;

di- or polyglycidyl ethers of polyhydric aliphatic alcohols such as 1,4-butanediol, or polyalkylene glycols such as polypropylene glycols; di- or polyglycidyl ethers of cycloaliphatic polyols such as 2,2-bis(4-hydroxycyclohexyl)propane; di- or polyglycidyl ethers of polyhydric phenols such as resorcinol, bis(4-hydroxyphenyl)methane (bisphenol F), 2,2-bis(4-hydroxyphenyl)propane (bisphenol A), 2,2-bis(4'-hydroxy-3',5'-dibromophenyl)propane, 1,1,2,2,-tetrakis(4'-hydroxyphenyl)ethane, or condensates of phenols with formaldehyde which are obtained under acid conditions, such as phenol novolaks and cresol novolaks; and also di- or poly($\beta$-methylglycidyl)ethers of the above polyalcohols and polyphenols; polyglycidyl esters and poly($\beta$-methylglycidyl)esters of polyvalent carboxylic acids such as phthalic acid, terephthalic acid, tetrahydrophthalic acid or hexahydrophthalic acid; N-glycidyl derivatives of amines, amides and heterocyclic nitrogen bases such as N,N-diglycidyl aniline, N,N-diglycidyl toluidine, triglycidyl isocyanurate, N,N,N',N'-tetraglycidyl bis(4-aminophenyl)methane, N,N'-diglycidyl ethyl urea, N,N'-diglycidyl-5,5-dimethylhydantoin, N'-diglycidyl-5-isopropylhydantoin, N,N'-diglycidyl-5,5-dimethyl-6-isopropyl-5,6-dihydrouracil.

Particularly preferred are polyglycidyl ethers of phenyl/formaldehyde or cresol/formaldehyde novolaks as well as diglycidyl ethers of bisphenol A and bisphenol F.

Examples of suitable catalysts (accelerators) are tertiary amines, salts or quaternary ammonium compounds thereof, e.g. benzyl dimethylamine, 2,4,6-tris(dimethylaminomethyl)phenol, 1-methylimidazole, 2-ethyl-4-methylimidazole, 2-phenylimidazole, 4-aminopyridine, tripentylammonium phenolate; or alkali metal alcoholates, e.g. sodium hexane triolate. The reaction (curing) of the compositions of the invention is conveniently carried out in the temperature range from 50°–300° C., preferably from 150°–300° C.

The preferred curing catalyst is 2-phenylimidazole.

Curing can be carried in known manner in two or more steps, the first step being carried out at low temperature and the postcuring at elevated temperature.

Two-step curing is normally carried out by first discontinuing the curing reaction prematurely, i.e. performing the first step at slightly elevated temperature, when a still fusible and/or soluble curable precondensate (B-stage) is obtained from the epoxy component (a) and the hardener component (b). Such a precondensate can be used e.g. for making prepregs, moulding compounds or sintering powders.

Surprisingly, the compositions of this invention comprising (a) an epoxy resin containing on average more than one epoxy group in the molecule, (b) at least one compound of formula I or II and (c) an optional curing accelerator, form soluble B-stages if these resin/hardener compositions are stored at room temperature. Such compositions are storage stable over prolonged periods of time (months) and can thus be employed as single component adhesive formulations.

The term "curing" as employed throughout this specification denotes the conversion of the soluble, either liquid or fusible, epoxy resins into solid insoluble and infusible three-dimensional cross-linked products or moulding materials, usually with concomitant shaping to moulded articles such as castings, mouldings and laminates, impregnations, coatings, varnish films or bonds.

The compositions of this invention can be prepared by simple stirring of the components and cautiously warming the components until dissolved. If a solid epoxy resin is used, this is temporarily heated to the melt and then the hardener and, optionally, the curing accelerator and/or other additives are dissolved in the melt.

Customary modifiers such as extenders, fillers and reinforcing agents, pigments, dyes, plasticisers, flow control agents, thixotropic agents, flexibilisers, flame retardants or mould release agents, can also be added, in any phase, to the curable mixtures of the present invention before curing.

Typical examples of extenders, reinforcing agents, fillers and pigments which may be added to the curable mixtures of this invention are: coal tar, bitumen, coumarone/indene resins, textile fibres, glass fibres, asbestos fibres, boron fibres, carbon fibres, cellulose, polyesters, polyamides, polyethylene powder, polypropylene powder, wood flour, quartz powder, mineral silicates such as mica, asbestos powder, slate powder, kaolin, silica aerogel, lithopones, barytes, titanium dioxide, carbon black, graphite, oxide colours such as iron oxide, or metal powders such as aluminium powder or iron powder.

Examples of suitable plasticisers for modifying the curable compositions ore dibutyl phthalate, dioctyl phthalate and dinonyl phthalate, tricresyl phosphate, trixylenyl phosphate and diphenoxyethylformal.

Examples of flow control agents which can be added when the curable mixtures are used in particular in surface protection are silicones, liquid acrylic resins, cellulose acetobutyrate, polyvinylbutyrate, waxes or stearates (some of which are also used as mould release agents).

Examples of suitable flexibilisers are oligoester segments, polyesters, thermoplasts and butadiene/acrylonitrile oligomers such as Hycar ® (a product of Goodrich).

The curable mixtures of this invention are distinguished by good storage stability, long processing times and good full hardening also in open curing in thin layer. The cured products possess excellent dimensional stability under heat and good resistance to hot water and chemicals. In particular, however, these products are distinguished by good resistance to hot water, which makes the curable compositions particularly interesting for use as adhesive formulations. A particularly surprising feature is the long-term resistance of bonds on storage in hot water.

The curable mixtures of this invention are used, in particular, in the fields of surface protection, electrical engineering, laminating processes and adhesives technology and in the building trade. They can be used in a formulation suited in each case to the particular application, in the unfilled or filled state, if desired in the form of solutions or emulsions, as paints, solvent-free coatings, whirl sintering powders, moulding compositions, casting resins, injection moulding compositions, impregnating resins, foams, adhesives, films, sheets, bonding agents, tooling resins, laminating resins, sealing and trowelling compounds, flooring compositions, and as binders for mineral aggregates.

In particular, the present invention relates to the use of compositions containing (a) an epoxy resin comprising on average more than one epoxy group in the molecule and (b) at least one compound of formula I and/or II as single component adhesive formulation.

PREPARATORY EXAMPLES (1a) o,o'-Bis(3-acetylthiopropyl)bisphenol A 666.8 g of 2,2-bis(3-allyl-4-hydroxyphenyl)propane are placed in a reaction vessel equipped with stirrer, dropping funnel and $N_2$ inlet and heated to 75° C. under a steady stream of $N_2$ gas. 4.92 g of azobisisobutyronitrile (AIBN) are then added and, through the dropping funnel, 780 g thioacetic acid are added over one hour. The temperature of the reaction mixture is maintained at 75° C. and 3 further 4.92 g portions of azobisisobutyronitrile are added every 20 minutes until a total of 19.68 g of AIBN has been added. The mixture is stirred at 75° C. under $N_2$ for 4 hours. A final portion of 4.92 g of azobisisobutyronitrile is added and the mixture is stirred for a further 3 hours. The product is then evaporated in a rotation vacuum evaporator (rotavap) to give 1036 g of a yellow paste.

(a) Microanalysis:

|  |  | C | H | S |
|---|---|---|---|---|
| theory | % | 65.19 | 7.00 | 13.92 |
| found | % | 64.5 | 6.96 | 13.2 |

(b) 100 MHz $^1$H-NMR spectrum

Absence of olefinic proton signals in the 5-6 ppm region (standard: TMS) indicate the complete disappearance of the allylic group Peaks at:
2.3 ppm (3 protons; —S—CO—CH$_3$)
1.8 ppm (2 protons; —S—C—CH$_2$—C-phenyl)
2.6 ppm (2 protons; —S—CH$_2$—C—C-phenyl)
2.8 ppm (2 protons; —S—C—C—CH$_2$-phenyl).

(1b) Purification of the crude product of Example (1a)

360.8 g of the crude pasty product of Example (1a) is dissolved in 100 ml hot xylene. 1 g of active charcoal is added and the solution is filtered and allowed to crystallize at 5° C. The crystals are filtered and dried under vacuum at 100° C. (50 mbar), affording 142 g of white crystals having a melting point of 118.1°–119.5° C.

Analysis of the pure recrystallized product (a) Microanalysis:

|  |  | C | H | S | O |
|---|---|---|---|---|---|
| theory | % | 65.19 | 7.00 | 13.92 | 13.89 |
| found | % | 65.88 | 7.07 | 13.43 | 13.79 |

(b) 250 MHz $^1$H-NMR spectrum
Peaks at (standard: TMS):

| chemical displacement (ppm) | 0.6 | 0.8 | 1.3 | 1.6 | 2.8 | 4.85 | 6.6–7.0 |
|---|---|---|---|---|---|---|---|
| number of protons (determined) | 6 | 4.5 | 6 | 4.1 | 4.2 | 2 | 6.3 |
| number of protons (expected) | 6 | 4 | 6 | 4 | 4 | 2 | 6 |
| peak inducing groups | —C(CH$_3$)$_2$— | —C—CH$_2$—C— | —S—CO—CH$_3$ | —C—CH$_2$—S—CO— | phenyl-CH$_2$—C—C— | —OH | phenyl |

(2a) Preparation of a (o-acetylthiopropyl)phenol/formaldehyde novolak

Following the procedure of Example 1, 419.9 g of a 2-allylphenol/formaldehyde novolak (allyl group content: 2.36 val) are reacted at 80° C., under nitrogen, with 179.9 g (2.36 moles) of thioacetic acid and 10.2 g of azobisisobutyronitrile. The azobisisobutyronitrile is added in 5 equal portions of 2.04 g. Yield: 589.2 g of product (98.2% of theory).

The $^1$H-NMR peaks (250 MHz) of the allyl protons of the starting material in the 5.1–5.2 ppm and 5.9–6.1 ppm range (against TMS) have disappeared from the $^1$H-NMR spectrum of the final product. Instead a peak of the protons of the acetyl group appears (at 2.3 ppm).

(2b) Purification of the crude product 200 ml of dichloromethane and 220 ml of aqueous ethanol (water content: 30% by volume) are added to 177.2 g of the crude product of Example 2a) and the supernatant phase is removed by decantation. A further 220 ml of aqueous ethanol and 100 ml of water are added and again the supernatant phase is removed by decantation. The residual novolak is washed twice with water and dried over Na$_2$SO$_4$. The product is subsequently dried again at 40° C. (17 mm Hg) and at 60° C. (3 mm Hg) in a rotary evaporator. Yield: 164 g of purified final product.

APPLICATION EXAMPLES

A. Determination of the adhesion of adhesive formulations on aluminium surfaces Adhesive formulations are prepared from the respective epoxy resin, the hardener and 2-phenylimidazole as curing catalyst. This comprises mixing the liquid epoxy resin at 85° C. with the hardener. After the hardener has dissolved, the mixture is cooled to 50° C. and the curing catalyst is added at 70° C. The mixture is then poured onto aluminium sheets and pulverised.

Adhesive bonds are then prepared with these formulations between the aluminium surfaces. This is done by punching bore holes of specific diameter and specific depth in an aluminium plate and filling them with the resin mixture. Aluminium cylinders of specific diameter are then fixed on this substrate. The adhesive bonds are then cured for 2 hours at 120° C.

Measurement of the adhesion of the bond is made with a Twistometer (q.v. Adhesion 3, edited by K. W. Allen; Applied Science Publishers Ltd., Barking (Essex); 1978). To this end the aluminium base plate is made fast and a specific torsional force is exerted by means of a lever arm. The adhesion can be ascertained from the maximum torsional force resulting in rupture of the adhesive bond.

Table 1 lists the values of the investigated liquid and solid epoxy adhesives which contain 2,2'-bis(3-acetylthiopropyl-4-hydroxyphenyl)propane (Example 1) as hardener. The table also indicates the glass transition temperatures $T_g$ of the cured adhesive compositions (determined by differential thermoanalysis).

Table 2 gives Twistometer data on epoxy adhesives containing different amounts of the 2-acetylthiopropylphenyl/formaldehyde novolak of Example 2 in combination with 2-phenylimidazole as curing catalyst. The table also indicates the viscosity of the mixture at 40° C.

TABLE 1

| Type of epoxy resin | Formulation (parts by wt) | | | molar ratio of hardener/ epoxide equivalent Δ | Adhesion (N/mm$^2$) | $T_g$* (°C.) |
| --- | --- | --- | --- | --- | --- | --- |
| | epoxy resin | hardener | curing catalyst | | | |
| liquid epoxy resin** | 100 | 61.75 | 0.25 | 0.25/1 | 62 | 57 |
| solid epoxy resin*** | 100 | 23.7 | 0.25 | 0.25/1 | 69.6 | 77 |

*higher $T_g$ values of the product (65.5° C. and 83° C. respectively) are obtained by curing in 2 hour cycles at 120° C., 150° C. and 180° C.
**epoxy resin based on bisphenol A; epoxide equivalent: 5.25 (val/kg); $\overline{M}_n$ = 350
***epoxy resin based on bisphenol A; epoxide equivalent: 2.0 (val/kg), $\overline{M}_n$ ~ 1000

TABLE 2

| Type of epoxy resin | Formulation (parts by wt) | | | Adhesion (N/mm$^2$) | $\eta^{40}$ (mPas) |
| --- | --- | --- | --- | --- | --- |
| | epoxy resin | hardener | curing catalyst | | |
| liquid epoxy resin* | 20 | 8.03 | 0.05 | 54.8 | 3410 |
| liquid epoxy resin* | 20 | 10.71 | 0.05 | 65.2 | 4051 |
| liquid epoxy resin* | 20 | 13.39 | 0.05 | 68.0 | 4660 |
| liquid epoxy resin* | 20 | 16.07 | 0.05 | 64.0 | 4700 |

*epoxy resin based on bisphenol A; epoxide equivalent: 5.25 (val/kg)

B. Determination of the adhesion of adhesive formulations on storage

An adhesive formulation consisting of 100 parts by weight of liquid epoxy resin (based on bisphenol A with an epoxide equivalent of 5.33 (val/kg), 61.34 parts by weight of 2,2'-bis(3-acetylthiopropyl-4-hydroxyphenyl)propane as hardener and 0.25 parts of 2-phenylimidazole as curing catalyst is prepared by mixing the resin and the hardener at 80° C. cooling the mixture to 50° C. and then adding the curing catalyst. The formulation is stored at 6° C. and at 20° C.

The epoxide equivalent of the mixture is measured at the different times (q.v. Kunststoffe 51, 714, 1961) as is also the adhesion of the cured mixture (q.v. Example A above).

Each of the adhesive bonds is cured for 2 hours at 120° C. before the torsion set. The results are reported in Table 3.

TABLE 3

| storage time (days) and (months) | Storage temperature | | | |
| --- | --- | --- | --- | --- |
| | 6° C. | | 20° C. | |
| | epoxide equivalent (Val/kg) | adhesion (N/mm$^2$) | epoxide equivalent (Val/kg) | adhesion (N/mm$^2$) |
| 0 | 3.33 | 66 ± 2.2 | 3.33 | 66 ± 2.2 |
| 8 | 3.16 | — | 2.81 | — |
| 57 | 2.74 | 62 ± 3 | 1.31 | 52 ± 6 |
| 7.5 months | — | — | 0.48 | 39 ± 10 |

C. Resistance to boiling water of Al/Al bonds

Adhesive formulations consisting of epoxy resin, hardener and curing catalyst are prepared (for amounts, see Table 4 below) by dissolving the liquid epoxy resin and the hardener (2,2'-bis(3-acetylthiopropyl-4-hydroxyphenyl)propane according to Example 1) at 85° C., cooling the mixture to 50° C. and adding the curing catalyst (2-phenylimidazole). When using a solid epoxy resin, the hardener is added at 100° C. and the curing catalyst at 70° C.

Al/Al bonds are prepared with these formulations. Curing is carried out for 2 hours at 120° C. and then for 30 minutes at 180° C. The criterion of the quality of the adhesive bonds is the shear strength according to DIN 53283 (on Anticordoal B). The samples are tested directly after curing or after specific intervals of time in cold and hot water storage. The results are reported in Table 4.

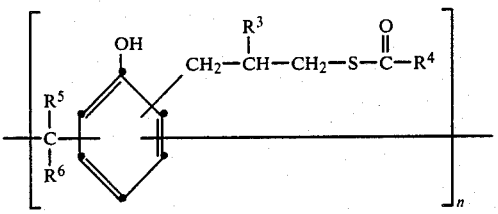

TABLE 4

| Type of epoxy resin | Formulation (parts by wt.) | | | Shear strength (N/mm$^2$) after storage (days) | | | | | | | |
| --- | --- | --- | --- | --- | --- | --- | --- | --- | --- | --- | --- |
| | | | | cold water storage (23° C.) | | | | hot water storage (90° C.) | | | |
| | resin | hardener | curing catalyst | 0 | 30 | 60 | 90 | 0 | 30 | 60 | 90 |
| liquid epoxy resin* | 100 | 62 | 0.25 | 20–22 | 15–17 | 15–17 | 13–16 | 20–22 | 18–20 | 16–19 | 16–18 |
| solid epoxy resin** | 100 | 25 | 0.25 | 21–23 | 18–20 | 18–21 | 17–20 | 21–23 | 21–23 | 19–21 | 18–21 |

*epoxy resin based on bisphenol A; epoxide equivalent = 5.25 (val/kg); $\overline{M}_n$ = 380
**epoxy resin based on bisphenol A; epoxide equivalent = 2.0 (val/kg); $\overline{M}_n \sim$ 1000

What is claimed is:

1. A compound of formula I or II

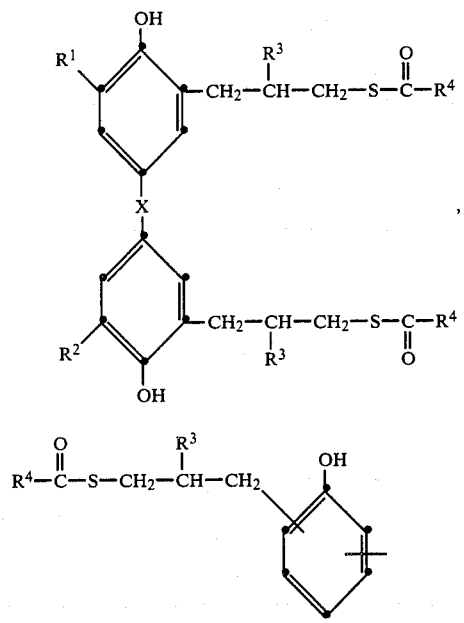

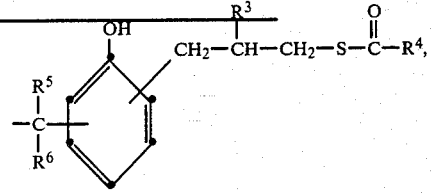

wherein $R^1$ and $R^2$ are each independently of the other hydrogen, $C_1$–$C_8$alkyl, cyclohexyl, phenyl, benzyl or tolyl, or are a —CH$_2$— CHR$^3$—CH$_2$—S—CO—R$^4$ radical, $R^3$ is hydrogen or methyl, $R^4$ is $C_1$–$C_{18}$-alkyl, cyclohexyl, phenyl, benzyl or tolyl, X is —CR$^5$R$^6$—, —S—, —SO—, —SO$_2$— or —(CH$_3$)C[—(CH$_2$)$_m$—COOR$^7$]—, in which $R^5$ and $R^6$ are each independently of the other hydrogen or $C_1$–$C_6$alkyl, $R^7$ is $C_1$–$C_{18}$alkyl, m is 1 or 2 and n is an integer from 1 to 10.

2. A compound of formula I or II according to claim 1, wherein $R^3$ is hydrogen.

3. A compound of formula I according to claim 1, wherein $R^1$ and $R^2$ are each independently of the other hydrogen or $C_1$–$C_{12}$alkyl, $R^3$ is hydrogen, $R^4$ is $C_1$–$C_4$alkyl, X is a —CR$^5$R$^6$ group, in which $R^5$ and $R^6$ are each independently of the other hydrogen or methyl.

4. A compound of formula I according to claim 1, wherein $R^1$, $R^2$ and $R^3$ are hydrogen, $R^4$ is methyl, and X is a group selected from —CH$_2$—, —CH(CH$_3$)— or —C(CH$_3$)$_2$.

5. A compound of formula I according to claim 1, wherein $R^1$ and $R^2$ are each independently of the other a —CH$_2$—CHR$^3$—CH$_2$—S—CO—R$^4$ group.

6. A compound of formula II according to claim 1, wherein $R^3$ is hydrogen, $R^4$ is methyl, —CR$^5$R$^6$— is a group selected from —CH$_2$—, —CH(CH$_3$)— or —C(CH$_3$)$_2$—, and n is an integer from 1 to 4.

7. A compound of formula II according to claim 1, wherein the —CH$_2$—CHR$^3$—CH$_2$—S—CO—R$^4$ groups are each ortho-positioned with respect to the phenolic hydroxyl group.

* * * * *